(12) United States Patent
Oates et al.

(10) Patent No.: US 8,367,669 B2
(45) Date of Patent: Feb. 5, 2013

(54) INHIBITORS OF HEMEPROTEIN-CATALYZED LIPID PEROXIDATION

(75) Inventors: John A. Oates, Nashville, TN (US); L. Jackson Roberts, II, Gallatin, TN (US); Ned A. Porter, Franklin, TN (US); Olivier Boutaud, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 1262 days.

(21) Appl. No.: 12/056,245

(22) Filed: Mar. 26, 2008

(65) Prior Publication Data

US 2008/0227776 A1    Sep. 18, 2008

Related U.S. Application Data

(63) Continuation-in-part of application No. 11/153,134, filed on Jun. 15, 2005, now abandoned.

(60) Provisional application No. 60/908,185, filed on Mar. 26, 2007.

(51) Int. Cl.

| | |
|---|---|
| *A01N 43/58* | (2006.01) |
| *A01N 43/54* | (2006.01) |
| *A01N 43/40* | (2006.01) |
| *A01N 43/42* | (2006.01) |
| *A61K 31/50* | (2006.01) |
| *A61K 31/435* | (2006.01) |
| *A61K 31/44* | (2006.01) |
| *C07D 239/42* | (2006.01) |
| *C07D 401/04* | (2006.01) |

(52) U.S. Cl. ......... 514/247; 514/256; 514/277; 514/279
(58) Field of Classification Search ............... 514/247, 514/256, 277, 279
See application file for complete search history.

(56) References Cited

U.S. PATENT DOCUMENTS

| | | | |
|---|---|---|---|
| 3,410,852 A | 11/1968 | Clauson-Kaas et al. |
| 3,947,416 A | 3/1976 | Beckwith |
| 4,188,487 A | 2/1980 | Los |
| 4,374,136 A | 2/1983 | Hill et al. |
| 4,554,276 A | 11/1985 | LaMattina |
| 4,711,888 A | 12/1987 | Walker |
| 4,726,837 A | 2/1988 | Hamprecht et al. |
| 4,871,848 A | 10/1989 | Treybig et al. |
| 4,968,673 A | 11/1990 | Humphrey |
| 5,001,136 A | 3/1991 | Walker |
| 5,128,359 A | 7/1992 | Bru-Magniez et al. |
| 5,137,881 A | 8/1992 | Hubsch et al. |
| 5,260,066 A | 11/1993 | Wood et al. |
| 5,284,949 A | 2/1994 | Belliotti et al. |
| 5,521,192 A | 5/1996 | Henrie et al. |
| 5,556,860 A | 9/1996 | Muraoka et al. |
| 6,140,499 A | 10/2000 | Fortunak |
| 6,835,216 B2 | 12/2004 | Pratt |
| 7,846,915 B2 | 12/2010 | Wong et al. |
| 7,939,548 B2 | 5/2011 | Lu et al. |
| 2002/0168366 A1 | 11/2002 | Stewart et al. |
| 2004/0209959 A1 | 10/2004 | Hogestatt et al. |
| 2005/0020511 A1 | 1/2005 | Li et al. |
| 2006/0009496 A1 | 1/2006 | Oates |
| 2006/0135447 A1 | 6/2006 | Chupak et al. |
| 2006/0194847 A1 | 8/2006 | Cheshire et al. |
| 2006/0205792 A1 | 9/2006 | Wong et al. |
| 2007/0054916 A1 | 3/2007 | Patel et al. |
| 2007/0238761 A1 | 10/2007 | Hudson et al. |
| 2008/0032973 A1 | 2/2008 | Hong et al. |
| 2008/0132545 A1 | 6/2008 | Lu et al. |
| 2008/0227776 A1 | 9/2008 | Oates et al. |
| 2008/0306053 A1 | 12/2008 | Tachdjian et al. |
| 2011/0053975 A1 | 3/2011 | Tazi et al. |

FOREIGN PATENT DOCUMENTS

| | | |
|---|---|---|
| DE | 2833274 | 2/1979 |
| DE | 3913757 | 10/1990 |
| JP | 09087296 | 3/1997 |
| JP | 2002146334 | 5/2002 |
| JP | 2002148801 | 5/2002 |

OTHER PUBLICATIONS

Mastaloudis, A.; Antioxidant supplementation prevents exercise-induced lipid peroxidation, but not inflammation, in ultramarathon runners; Free Radic. Biol. Med.; 2004; 36(10); pp. 1329-1341 (abstract).

Wilcox, et al.,; Dietary flavonoids fail to suppress F2-isoprostane formation in vivo; Free Radic. Biol. Med.; 2003; 34 (7); pp. 795-799 (abstract).

Morrow, Jason; Is oxidant stress a connection between obesity and atherosclerosis?; Arterioscler. Thromb. Vasc. Biol.; 2003; 23; pp. 368-370.

Ikizler, et al.; Plasma Fs-isoprostane levels are elevated in chronic hemodialysis patients; Clin. Nephrol.; 2002; 58(3); pp. 190-197 (abstract).

Morrow, et al.; Marked overproduction of non-cyclooxygenase derived prostanoids (F2-isoprostanes) in the hepatorenal syndrome; J. Lipid Mediat.; 1993; 6(1-3); pp. 417-420.

Reeder, et al.; Toxicity of myoglobin and haemoglobin: oxidative stress in patients wtih rhabdomyolysis and subarachnoid haemorrhage; Biochem. Soc. Transations; 2002; 30(4); pp. 745-748.

Nenseter, et al.; Paracetamol inhibits copper ion-inducted, azo compound-initiated and mononuclear cell-mediated oxidative modification of LDL; Arterscler. Thromb. Vasc. Biol; 1995; 15; pp. 1338-1344.

Davi, et al.; In vivo formation of 8-iso-prostaglandin F2a and platelet activation in diabetes mellitus. Effects of improved metabolic control and Vitamin E Supplemenation; Circulation; 1999; 99; pp. 224-229.

Sakamoto, et al.; Isoprostanes-markers of ischaemia reperfusion injury; Eur. J. Anaesthesiol.; 2002; 19(8); pp. 550-559 (abstract—PubMed ID 12200943).

Holt, et al.; Increased lipid peroxidation in patients with rhabdomyolysis; The Lancet; 1999; 353; pp. 1241.

Golfetti, et al.; Chronically administered acetaminophen and the ischemia/reperfused mycardium; Exp. Biol. Med; 2003; 228; pp. 674-682.

(Continued)

Primary Examiner — Yong Chong
(74) Attorney, Agent, or Firm — Stites & Harbison PLLC; Richard S. Myers, Jr.

(57) ABSTRACT

Methods and compounds for the treatment or prevention of oxidative damage in a mammalian subject. The treatment and/or prevention may be on inhibiting heme-induced lipid peroxidation. Also discloses are methods and compounds for treating or preventing isoprostane-mediated tissue damage.

11 Claims, 5 Drawing Sheets

OTHER PUBLICATIONS

Merrill, et al.; Antioxidant properties of acetaminophen and cardioprotection; Basic Res. Cardio.; 2001; 96; pp. 423-430.

Morrow, et al.; Marked overproduction of non-cyclooxygenase derived prostanoids (F2-isoprostanes) in the hepatorenal syndrome; J. Lipid Mediators; 1993; 6; pp. 417-420.

Morrow, et al.; A series of prostaglandin F2-like compounds are produced in vivo in humans by a non-cyclooxygenase, free radical-catalyzed mechanism; Proc. Natl. Acad. Sci USA; 1990; 87: pp. 9383-9387.

Morrow, et al.; Non-cyclooxygenase-derived prostanoids (F2-isoprostanes) are formed in situ on phospholipids; Proc. Natl. Acad. Sci USA; 1992; 89; pp. 10721-10725.

Takahashi, et al.; Glomerular actions of a free radical-generated novel prostaglandin, 8-epi-prostaglandin F2a in the rat evidence for interaction with thromboxane A2 receptors; J. Clin. Invest.; 1992; 90; pp. 136-141.

Dietrich, et al.; Antioxidant supplementation decreases lipid peroxidation biomarker F2-isoprostanes in plasma of smokers; Cancer Epidemiol. Biomarkers & Prevention; 2002; 11; pp. 7-13.

Klein, et al.; Generation of the isoprostane 8-epi-prostaglandin F2a in vitro and in vivo via the cyclooxygenases; J. Pharmacol. Exp. Therapeutics; 1997; 282(3); pp. 1658-1665.

Boutaud, et al.; Determinants of the cellular specificity of acetaminophen as an inhibitor of prostaglandin H2 synthases; Proc. Natl. Acad. Sci USA; 2002; 99(10); pp. 7130-7135.

Moore, et al.; A causative role for redox cycling of myoglobin and its inhibition by alkalinization in the pathogenesis and treatment of rhabdomyolysis-induced renal failure; J. Biol. Chem.; 1998; 273(48); pp. 31731-31737.

Lawson, et al.; Isoprostanes: Formation, analysis and use as indices of lipid peroxidation in vivo; J. Biol. Chem.; 1999; 274(35); 24441-24444.

Chiabrando, et al.; Long-term Vitamin E supplementation fails to reduce lipid peroxidation in people at cardiovascular risk: Analysis of underlying factors; Curr. Controlled Trials Cardiovasc. Med.; 2002; 3; pp. 5.

Sciulli, et al.; Effects of Acetaminophen on Constitutive and Inducible Prostanoid Biosynthesis in Human Blood Cells; Br. J. Pharmacol.; 2003; 138; pp. 634-641.

Jeney, et al.; Pro-oxidant and cytotoxic effects of circulating heme; Blood; 2002; 100(3); pp. 879-887.

Janssen, et al.; Involvement of TP and EP3 receptors in vasoconstrictor responses to isoprostanes in pulmonary vasculature; J. Pharmacol. Exp. Therapeutics; 2002; 301(3); pp. 1060-1066.

Paller, Mark; Hemoglobin- and Myoglobin-induced acute renal failure in rats: Role of iron in nephrotoxicity; Am. J. Physiol.; 1988; 255 (Renal Fluid Electrolyte Physiol. 24); F539-F544.

Colletti, et al.; Effects of Acetaminophen and Ibuprofen on renal function in anaesthetized normal and sodium-depleted dogs; J. Appl. Physiol.; 1999; 86(2); pp. 592-597.

Holt, et al.; Pathogenesis of renal failure in rhabdomyolysis: the role of myoglobin; Exp. Nephrol; 2000; 8(2) pp. 72-76 (abstract).

Merrill, et al.; Coronary and myocardial effects of acetaminophen: protection during ischemia-reperfusion; Am. J. Physiol. Heart Circ. Physiol.; 2001; 280; pp. H2631-H2638.

Alayash, Abdu; Oxygen therapeutics: can we tame haemoglobin?; Nat Rev Drug Discov; 2004; 3(2); pp. 152-159.

Farquhar, et al.; Effects of acetaminophen and ibuprofen on renal function in the stressed kidney; J. Appl. Physiol.; 1999; 86(2); pp. 598-604.

Barada, Kassem; Hepatorenal syndrome: pathogenesis and novel pharmacological targets; Curr. Opin. Pharmacol; 2004; 4: pp. 189-197.

Klings, et al.; Increased F2 isoprostanes in the acute chest syndrome of sickle cell disease as a maker of oxidative stress; Am. J. Respir. Crit. Care Med; 2001; 164: pp. 1248-1252.

Basu, et al.; Raised levels of F2-isoprostanes and prostaglandin F2a in different rheumatic diseases; Ann Rheum Dis; 2001; 60; pp. 627-631.

Janssen, L.J.; Isoprostanes: an overview and putative roles in pulmonary pathophysiology; Am J. Physiol Cell Mol Physiol; 2001; pp. L1067-L1082.

Golfetti, et al.; Acetaminophen in the post-ischemia reperfused myocardium; Exp Biol Med; 2002; 227; pp. 1031-1038.

Kapiotis, et al.; Paracetamol catalyzes myeloperoxidase-initiated lipid oxidation in LDL; Arteriosclerosis, Thrombosis, Vasc Biol; 1997: 17; pp. 2855-2860.

Morrow, J.; Quantification of F2-isoprostanes as an index of lipid peroxidation in vitro and in vivo uses and controversies; Powerpoint presentation posted on national cancer institute/center for cancer research website: http: ccr.cancer.gov/faculties/docs.asp?facid=452.

Wijtmans, et al.; Synthesis and reactivity of some 6-substituted-2, 4-dimethyl-3-pyridinols, a novel class of chain-breaking antioxidants; J. Org. Chem.; 2004; 69; pp. 9215-9223.

Morrow, et al.; Free radical-induced generation of isoprostanes in vivo; J. Biol. chem.; 1994; 269(6); pp. 4317-4326.

Jankov, et al.; Thromboxane A2 receptors mediate pulmonary hypertension in 60% oxygen-exposed newborn rats by a cyclooxygenase-independent mechanism; Am J Respir Crit Care Med; 2002; 166; pp. 208-214.

Morrow, et al.; The isoprostanes: their role as an index of oxidant stress status in human pulmonary disease; Am J Resp Crit Care Med; 2002; 166; pp. S25-S30.

Cracowski, et al.; Isoprostanes, emerging biomarkers and potential mediators in cardiovascular diseases; Eur Heart J.; 2004; 25; pp. 1675-1678.

Rao, et al.; The role of iron in prostaglandin synthesis: ferrous iron mediated oxidation of arachidonic acid; Prostaglandins Med; 1978; 1(1); pp. 55-70.

Roberts, et al.; Acetaminophen reduces ferryl myoglobin and prevents rhabdomyolysis-induced renal failure; Abstract presented by Society for Free Radical Biology and Medicine Annual Meeting, Nov. 17-21, 2004.

Moore, et al.; A causative role for redox cycling of myoglobin and its inhibition by alkalinization in the pathogenesis and treatment of rhabdomyolysis-induced renal failure; J. Biol Chem; 1998; 273(48); pp. 31731-31737.

Basu, S. et al., "Raised Levels of F2-Isoprostanes and Prostaglandin F20 in Different Rheumatic Diseases," Ann Rheum Dis 60, 627-631 (2001).

Frankel et al., "Inhibition of Human LDL Oxidation by Resveratrol," The Lancet 341:1103-4, Apr. 24, 1993.

Goldberg et al., Anal. Chem. "Direct Injection Gas Chromatographic Mass Spectrometric Assay for trans-Resveratrol," 66: 3959-63, 1994.

Goldberg et al., A Global Survey of Trans-Resveratrol Concentrations in Commercial Wines, Am. J. Enol. Vitic. 46 (2): 159-165, 1995.

Hess et al., Systemic and pulmonary hypertension after resuscitation with cell-free hemoglobin, J. Appl Physiol, 74: 1769-1778, 1993.

Jang et al., "Cancer Chemopreventive Activity of Resveratrol, a Natural Product Derived from Grapes," Science 275:218-220, 1997.

Jeandet et al., The Production of Resveratrol (3,5,4'-trihydroxystilbene) by Grape Berries in Different Developmental Stages, Am. J. Enol. Vitic. 42:41-46, 1991.

Lee et al., Protection of Cell Injury Against Oxidative Stress by Resveratrol, Society for Neuroscience Abstracts 20 (1-2):1648, 1994 [Abstract Only].

Moreno-Manas et al., Dehydroacetic acid chemistry, a new synthesis of resveratrole, a phytoalexine of *Vitis vinifera*, Anal. Quim. 81:157-161 (1985).

Ogletree, Martin L., et al., "Pharmacological Profile of BMS 180,291: A Potent, Long-Acting, Orally Active Thromboxane A2/Prostaglandin Endoperoxide Receptor Antagonist", The Journal of Pharmacology and Experimental Therapeutics, vol. 264, No. 2, pp. 570-578.

Pace-Asciak et al., "The red wine phenolics trans-resveratrol and quercetin block human platelet aggregation and eicosanoid synthesis: Implications for protection against coronary heart disease," Clinica Chimica Acta 235:207-219 (1995).

Seibert et al., Role of Inducible Cyclooxygenase (COX-2) in Inflammation, Receptor, 4:17-23, 1994.-

Soleas et al., A Derivatized Gas Chromatographic-Mass Spectrometric Method for the Analysis of Both Isomers of Resveratrol in Juice and Wine, Am. J. Enol. Vitic 46(3): 346-352, 1995.

Yamashita, W. et al., A thromboxane synthetase antagonist ameliorates progressive renal disease of Dahl-S rats, Kidney Intl. 33: 77-83, 1988.

Tazzeo, T. et al., Vasoconstrictor responses, and underlying mechanisms, to isoprostanes in human and porcine bronchial arterial smooth muscle, British Journal of Pharmacology, 140(4) 759-763 (2003).

Mezzetti, A. et al., Oxidative stress and cardiovascular complications in diabetes: isoprostanes as new markers on an old paradigm, Cardiovascular Res. 2000, 47(3) 475-488.

Pattichis et al., "Phenolic substances in red wine and release of platelet 5-hydroxytryptamine," The Lancet 341:1104, Apr. 24, 1993.

INHIBITORS OF HEMEPROTEIN-CATALYZED LIPID PEROXIDATION

PRIORITY INFORMATION

This application is a continuation-in-part of U.S. patent application Ser. No. 11/153,134, filed Jun. 15, 2005 now abandoned; and claims benefit to U.S. Patent Application No. 60/908,185, filed Mar. 26, 2007. The content of both applications is incorporated herein by reference.

GOVERNMENT SUPPORT

This invention was made in part with funding provided by grant numbers GM015431 and GM042056 by the National Institutes of Health. The United States Government has certain rights to this invention.

FIELD OF THE INVENTION

The present invention relates, generally, to the field of hemeprotein-catalyzed lipid peroxidation, and methods of inhibiting the formation of hemo-protein and heme-mediated oxidation products and methods for preventing tissue and organ damage associated with hemoprotein and heme-mediated oxidation and oxidation products.

Additionally, the present invention relates to the field of COX-1 and COX-2 inhibition, and methods of treating cyclooxygenase mediated indications and/or diseases, including the treatment or alleviation of inflammation and other inflammation associated disorders such as arthritis and neurodegeneration.

BACKGROUND OF THE INVENTION

Oxidative stress has been associated with a number of disease states, including cardiovascular disorder disorders, neurological disorders, cancer, and diabetes. Heme acts as a pro-inflammatory molecule involved in the pathology of conditions as diverse as renal failure, arteriosclerosis, and peritoneal endometriosis.

Although correlations have been found between lipid peroxidation and a wide variety of seemingly diverse diseases, and certain oxidized lipids have also been proposed as markers, which would indicate the presence of or level of oxidative damage, it would be of great value to identify the biochemical processes that produce such oxidative damage and to identify pharmaceutical agents that may prevent it.

Cyclooxygenase is an enzyme that catalyzes a rate-determining step in the biosynthesis of prostaglandins, which are important mediators of inflammation and pain. The enzyme occurs as at least two distinct isomers, cyclooxygenase-1 (COX-1) and cyclooxygenase-2 (COX-2). The COX-1 isomer is constitutively expressed in the gastric mucosa, platelets and other cells and is involved in the maintenance of homeostasis in mammals, including protecting the integrity of the digestive tract. The COX-2 isomer, on the other hand, is not constitutively expressed but rather is induced by various agents, such as cytokines, mitogens, hormones and growth factors. In particular, COX-2 is induced during the inflammatory response (DeWitt D L, Biochim Biophys Acta, 1083: 121-34, 1991; Seibert et al., Receptor, 4:17-23, 1994.). Aspirin and other conventional non-steroid anti-inflammatory drugs (NSAIDs) are non-selective inhibitors of both COX-1 and COX-2. They can be effective in reducing inflammatory pain and swelling, but they produce undesirable side effects of gastrointestinal pathology.

Thus, NSAIDs are widely used in treating pain and the signs and symptoms of arthritis because of their analgesic and anti-inflammatory activity because of the acceptance that they work by blocking the activity of cyclooxygenase (COX), also known as prostaglandin G/H synthase (PGHS), the enzyme that converts arachidonic acid into prostanoids. Prostaglandins, especially prostaglandin $E_2$ ($PGE_2$), which is the predominant eicosanoid detected in inflammation conditions, are mediators of pain, fever and other symptoms associated with inflammation. Inhibition of the biosynthesis of prostaglandins has been a therapeutic target of anti-inflammatory drug discovery. The therapeutic use of conventional NSAIDs is, however, limited due to drug associated side effects, including life threatening ulceration and renal toxicity. An alternative to NSAIDs is the use of corticosteriods, however, long term therapy can also result in severe side effects.

DESCRIPTION OF THE INVENTION

Figure 1:
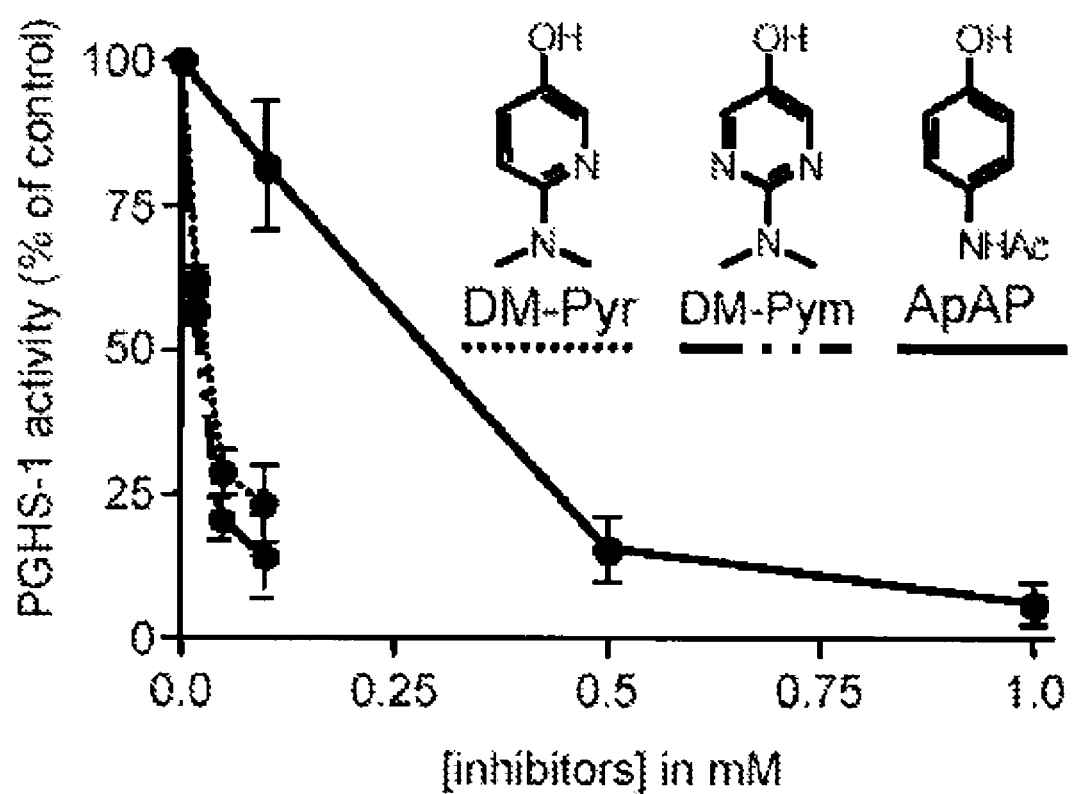
FIG. 1 is a graph that shows inhibition of PGHS-1 by N-dimethyl pyridinol and N-dimethylpyrimidinol analogues of acetaminophen (ApAP).

As indicated above, the presently disclosed invention discloses compounds, compositions, and methods of using said compounds and compositions.

With respect to the present invention, the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

Following long-standing patent law convention, the terms "a", "an", and "the" mean "one or more" when used in this application, including the claims. Thus, for example, the phrase "a reactive oxygen species" refers to one or more reactive oxygen species.

The term "about", as used herein when referring to a measurable value such as an amount of weight, time, dose (e.g., a dose of a compound of the present invention), etc., is meant to encompass variations of in some embodiments +/−20%, in some embodiments +/−10%, in some embodiments +/−5%, in some embodiments 1%, and in some embodiments +/−0.1% from the specified amount, as such variations are appropriate to perform the disclosed methods.

As used herein, the term "and/or" refers to alternatives in which one or more of the listed entities is present. For example, the phrase "A and/or B" refers to alternatives wherein A is present, B is present, or both A and B are present. In those cases where more than two alternatives are present, the phrase "and/or" refers to alternatives in which any one of the listed entities is present, all of the listed entities are present, or any subset of listed entities is present.

As used herein, the phrase "associated with" refers to a relationship between two or more occurrences that one of ordinary skill in the art would recognize is normally or frequently observable when one or more of the occurrences is present. For example, a "symptom associated with a disorder in a subject" is a symptom that is normally, frequently, or sometimes present in the subject when the subject has the disorder. It is understood, however, that the symptom need not necessarily be indicative of the disorder, causative of the disorder, or absent in the subject in the absence of the disorder. Thus, the phrase "associated with" does not necessarily imply a causal relationship between the two or more occurrences, although in some embodiments a causal relationship can exist.

For example, in some embodiments the phrase "kidney disorder that is associated with oxidative stress, carbonyl stress, or combinations thereof" refers to any nephropathy at least one symptom of which is caused by or modulated by oxidative stress, carbonyl stress, or combinations thereof, as those terms would be understood by one of ordinary skill in the art after review of the instant disclosure. In some embodiments, a "kidney disorder that is associated with oxidative stress, carbonyl stress, or combinations thereof" is a medical condition associated with elevated levels of reactive carbonyl species (RCS), reactive oxygen species (ROS), and/or advanced glycation end products (AGE). In some embodiments, a "kidney disorder that is associated with oxidative stress, carbonyl stress, or combinations thereof" comprises acute renal injury (ARI), acute renal failure (ARF), and combinations thereof.

As used herein with respect to compositions comprising compounds of the present invention, the phrase "effective amount" refers to an amount of compounds and/or compositions of the present invention that when administered to a subject as a single dose or in multiple doses leads to an amelioration of (e.g., an improvement of, a decreased duration of, etc.) at least one symptom of a disorder disclosed herein. In some embodiments, the disorder and/or the symptom is associated with oxidative stress, carbonyl stress, or combinations thereof in the subject. In some embodiments, the effective amount reduces formation of, reactivity of, or both formation and reactivity of at least one RCS, ROS, or AGE in order to ameliorate at least one symptom of the disease associated with oxidative stress, carbonyl stress, or combinations thereof in the subject.

Oxidative stress is the term used to describe a physiological state that can promote and/or can be associated with an increase in the level of reactive oxygen species (ROS) and reactive nitrogen species (NOS), either from injury or disease processes, or a decrease in endogenous protective anti-oxidative capacity, or both. Oxidative stress is usually accompanied by carbonyl stress characterized by an increase in production of low molecular weight reactive carbonyl species (RCS). In many types of illnesses, including but not limited to sepsis, trauma, burn injury, acute pancreatitis, liver injury, severe diabetes, acute respiratory distress syndrome, AIDS, and acute renal failure, increased oxidative stress and/or carbonyl stress can occur.

As used herein, the term "treatment", and grammatical variants thereof, refers to a medical intervention that is designed to reduce or eliminate at least one symptom resulting from a disease process as described herein. The term "prevention", and grammatical variants thereof, refers to a medical intervention that is designed to retard or prevent the initial development or subsequent progression of at least one symptom resulting from a disease process as described herein. Thus, in some embodiments "prevention" and "treatment" can overlap. As such, the terms are used substantially interchangeably herein, although it is understood that "treatment" implies that at least one symptom resulting from a disease process as disclosed herein has become manifest in some observable and/or quantifiable fashion.

In some embodiments, the methods disclosed herein provide for treatment and/or prevention of acute renal failure and/or acute renal injury in a subject. As used in this context, the term "prevent" is also intended to relate to a prophylactic approach, such that "preventing" includes both modulating the initial development of a disease process as well as modulating the further development of (i.e., the worsening of) a disease process. It is understood that the degree of prevention/prophylaxis need not be absolute (e.g., complete prevention of the development of a disease process such that the subject does not develop the disease process at all), and that intermediate levels of prevention/prophylaxis including, but not limited to increasing the time required for at least one symptom resulting from a disease process to develop, reducing the severity of at least one symptom resulting from a disease process, and reducing the time that at least one symptom resulting from a disease process is present within the subject are all examples of prevention/prophylaxis. With respect to the latter two circumstances, these are examples wherein "prevention/prophylaxis" and "treatment" can be considered to coincide.

It is also understood that the disclosed methods can be used as part of a combination therapy, and need not be employed as the sole therapy to address a disease process as disclosed herein.

As used herein, the term "alkyl" means $C_{1-12}$, inclusive (i.e., carbon chains comprising 1, 2, 3, 4, 5, 6, 7, 8, 9, 10, 11, or 12 carbon atoms; also, in some embodiments, $C_{1-6}$ inclusive) linear, branched, or cyclic, saturated or unsaturated (i.e., alkenyl and alkynyl) hydrocarbon chains, including for example, methyl, ethyl, propyl, isopropyl, butyl, isobutyl, tert-butyl, pentyl, hexyl, ethenyl, propenyl, butenyl, pentenyl, hexenyl, butadienyl, propynyl, butynyl, pentynyl, hexynyl, and allenyl groups.

The alkyl group can be optionally substituted with one or more alkyl group substituents which can be the same or different, where "alkyl group substituent" includes alkyl, halo, aryl, arylamino, acyl, hydroxy, aryloxy, alkoxyl, alkylthio, arylthio, aralkyloxy, aralkylthio, carboxy, alkoxycarbonyl, oxo, and cycloalkyl. In this case, the alkyl can be referred to as a "substituted alkyl". Representative substituted alkyls include, for example, benzyl, trifluoromethyl, and the like. There can be optionally inserted along the alkyl chain one or more oxygen, sulfur or substituted or unsubstituted nitrogen atoms, wherein the nitrogen substituent is hydrogen, alkyl (also referred to herein as "alkylaminoalkyl"), or aryl. Thus, the term "alkyl" can also include esters and amides. "Branched" refers to an alkyl group in which an alkyl group, such as methyl, ethyl, or propyl, is attached to a linear alkyl chain.

Administration can be by any method known to one of ordinary skill in the art. In some embodiments, suitable methods for administration of compounds of the present invention include, but are not limited to intravenous administration, bolus injection, and oral administration.

An effective dose for use in the presently disclosed methods is administered to a subject in need thereof. Thus, in addition to above, the phrase "effective amount" can also refer to an amount of a therapeutic composition of the present invention sufficient to produce a biologically or clinically relevant response (e.g., a "benefit") in a subject being treated. The actual amount delivered can be varied so as to administer an amount that is effective to achieve the desired therapeutic response for a particular subject.

The potency of a composition can vary, and therefore an "effective amount" can vary. However, using standard assay methods, one skilled in the art can readily assess the potency and efficacy of the present invention, and adjust the therapeutic regimen accordingly.

After review of the disclosure of the presently disclosed subject matter presented herein, one of ordinary skill in the art can tailor the dosages to an individual subject, taking into account the particular formulation, method of administration to be used with the composition, and particular disease process to be treated and/or prevented. Further calculations of dose can consider subject height and weight, severity and stage of symptoms, and the presence of additional deleterious physical conditions. Such adjustments or variations, as well as evaluation of when and how to make such adjustments or variations, are well known to those of ordinary skill in the art of medicine. In some embodiments, the effective amount is selected from the group consisting of less than 1 mg/day, about 1-10 mg/day, about 10-50 mg/day, about 50-100 mg/day, about 100-200 mg/day, about 200-300 mg/day, about 300-400 mg/day, about 400-500 mg/day, and more than 500 mg/day.

As is known in the art, these dosages can be administered at one time or as part of two or more daily administrations. For example, for oral administration, the dose can be in some embodiments about 50 mg/dose bid in die (BID), in some embodiments about 100 mg/dose BID, and in some embodiments about 250 mg/ml BID. For intravenous administration, the daily dose can be in some embodiments about 25 mg/day, in some embodiments about 50 mg/day, and in some embodiments about 200 mg/day. It is understood that the effective amount might vary among patients, and further that the actual dose administered can easily be modified by a physician as needed.

One of ordinary skill in the art will appreciate that the compounds of the invention are useful in treating a diverse array of diseases. One of ordinary skill in the art will also appreciate that when using the compounds of the invention in the treatment of a specific disease that the compounds of the invention may be combined with various existing therapeutic agents used for that disease.

The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flurbiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib and rofecoxib, analgesics and intraarticular therapies such as corticosteroids and hyaluronic acids such as hyalgan and synvisc.

The active ingredient of the present invention may be also administered in combination with inhibitors of other mediators of inflammation, comprising one or more members selected from the group consisting essentially of the classes of such inhibitors and examples thereof which include, matrix metalloproteinase inhibitors, aggrecanase inhibitors, TACE inhibitors, IL-1 processing and release inhibitors, ILra, $H_1$-receptor antagonists; kinin-$B_1$- and $B_2$-receptor antagonists; prostaglandin inhibitors such as PGD-, PGF-$PGI_2$-, and PGE-receptor antagonists; thromboxane $A_2$ (TXA2-) inhibitors; 5- and 12-lipoxygenase inhibitors; leukotriene $LTC_4$-, $LTD_4/LTE_4$-, and $LTB_4$-inhibitors; PAF-receptor antagonists; gold in the form of an aurothio group together with various hydrophilic groups; immunosuppressive agents, e.g., cyclosporine, azathioprine, and methotrexate; anti-inflammatory glucocorticoids; penicillamine; hydroxychloroquine; anti-gout agents, e.g., colchicine, xanthine oxidase inhibitors, e.g., allopurinol, and uricosuric agents, e.g., probenecid, sulfinpyrazone, and benzbromarone.

The compounds of the present invention may also be used in combination with anticancer agents such as endostatin and angiostatin or cytotoxic drugs such as adriamycin, daunomycin, cis-platinum, etoposide, taxol, taxotere and alkaloids, such as vincristine, and antimetabolites such as methotrexate.

The compounds of the present invention may also be used in combination with anti-hypertensives and other cardiovascular drugs intended to offset the consequences of atherosclerosis, including hypertension, myocardial ischemia including angina, congestive heart failure, and myocardial infarction, selected from diuretics, vasodilators such as hydralazine, .beta.-adrenergic receptor antagonists such as propranolol, angiotensin-II converting enzyme inhibitors (ACE-inhibitors) such as enalapril used to treat geriatric mammals with mitral insufficiency, and enalapril alone and in combination with neutral endopeptidase inhibitors, angiotensin II receptor antagonists such as losartan, renin inhibitors, calcium channel blockers such as nifedipine, $\alpha_2$-adrenergic agonists such as clonidine, $\alpha$-adrenergic receptor antagonists such as prazosin, and HMG-CoA-reductase inhibitors (anti-hypercholesterolemics) such as lovastatin or atorvastatin.

The active ingredient of the present invention may also be administered in combination with one or more antibiotic, antifungal, antiprotozoal, antiviral or similar therapeutic agents.

The compounds of the present invention may also be used in combination with CNS agents such as antidepressants (such as sertraline), anti-Parkinsonian drugs (such as L-dopa, requip, miratex, MAOB inhibitors such as selegine and rasagiline, comP inhibitors such as Tasmar, A-2 inhibitors, dopamine reuptake inhibitors, NMDA antagonists, nicotine agonists, dopamine agonists and inhibitors of neuronal nitric oxide synthase), and anti-Alzheimer's drugs such as donepezil, tacrine, COX-2 inhibitors, propentofylline or metrifonate.

The compounds of the present invention may also be used in combination with osteoporosis agents such as roloxifene, droloxifene or fosomax and immunosuppressant agents such as FK-506 and rapamycin.

This invention also relates to method for treating or preventing diseases or conditions mediated by cyclooxygenase-2 in a mammal comprising administering an amount of a compound according to claim 1 or a pharmaceutically acceptable salt thereof effective for treating said diseases or conditions to said mammal.

This invention also relates to a pharmaceutical composition comprising an amount of a compound of the present invention or a pharmaceutically acceptable salt thereof effective for treating or preventing diseases or conditions mediated by cycloxygenase-2.

More specifically, this invention relates to a pharmaceutical composition for treating a disease, or condition selected from the group consisting of diseases or conditions in which prostaglandins are implicated as pathogens, pain, fever, inflammation, rheumatic fever, symptoms associated with influenza and other viral infections, common cold, low back and neck pain, dysmenorrhea, headache, toothache, sprains and strains, myositis, neuralgia, synovitis, arthritis including rheumatoid arthritis, degenerative joint disease or osteoarthritis, gout and ankylosing spondylitis, bursitis, burns, injuries following surgical and dental procedures, disease or conditions associated with cellular neoplastic transformations and metastic tumor growth, cancer, colorectal cancer, breast and skin cancer, familiar adenomatous polyposis, cyclooxygenase-mediated proliferation disorders, cyclooxygenase-mediated proliferation disorders in diabetic retinopathy and tumor angiogenesis, prostaniod-induced smooth muscle contraction mediated by synthesis of contractile prostanoids, dysmenorrhea, premature labor, asthma, eosinophil related disorders, neurodegenerative diseases, Alzheimer's and Parkinson's disease, bone loss, osteoarthritis, peptic ulcers, gastritis, regional enterotis, ulcerative colitis, diverticulitis, recurrent of gastrointestinal lesions, gastrointestinal bleeding, coagulation, anemia, hypoprothrombinemia, haemophilia, bleeding problems; kidney disease and conditions prior to surgery of taking of anticoagulants.

This invention also relates to a pharmaceutical composition comprising an amount of a compound of the present invention or a pharmaceutically acceptable salt thereof effective for inhibiting hemeprotein-catalyzed lipid peroxidation.

Acetaminophen, with selective analgesic and anti-pyretic effects, is among the most widely used drugs in the world. Yet there is growing concern for the hepatotoxicity of the drug and toxicologists in the U.K. predict that the drug would be removed from that market in the event of a safe and effective alternative.

Acetaminophen acts by blocking biosynthesis of prostaglandins selectively in cells that are in the signaling pathway for fever and pain. The prostaglandin H synthases (PGHS; cyclooxygenases) that catalyze formation of the prostaglandins are bifunctional enzymes with peroxidase and cyclooxygenase active sites. Reduction of a hydroperoxide in the peroxidase site generates a protoporphyrin radical that leads to formation of a tyrosyl radical in the cyclooxygenase site. This tyrosyl radical then initiates the oxygenation of arachidonic acid that results in prostaglandin formation. This enzyme, therefore, functions essentially as a hemoprotein that catalyzes structurally specific lipid oxygenation. Acetaminophen has been known to reduce the PGHS protoporphyrin radical, and our recent work has demonstrated that acetaminophen acts to inhibit prostaglandin formation selectively in cells in which the concentration of hydroperoxides is low enough to permit acetaminophen to maintain the enzyme in a reduced and catalytically inactive state. The compounds of the present invention, as inhibitors of hemoprotein-catalyzed lipid peroxidation are markedly more potent than acetaminophen as inhibitors of the PGHSs, and cell based toxicology studies indicate that lead compounds are likely to be free of the hepatotoxicity produced by acetaminophen.

The compounds if the present invention, therefore, are attractive for other important indications.

One embodiment of the present invention relates to the treatment of subarachnoid hemorrhage with inhibitors of hemeprotein-catalyzed lipid peroxidation.

Aneurysmal subarachnoid hemorrhage (SAH) is an often devastating form of stroke with high morbidity and mortality despite advances in surgical management. Approximately 30,000 patients annually suffer from SAH in the U.S., and the worldwide annual incidence approaches 400,000. For patients who survive the initial subarachnoid hemorrhage, delayed cerebral vasospasm occurring from days 4-14 is the greatest cause of neurological disability and death.

A growing body of evidence incriminates hemoprotein-catalyzed lipid peroxidation as the mediator of the vasospasm. Hemoglobin released from lysed red cells in the subarachnoid space becomes oxidized, in which state it acts as a pseudoperoxidase and generates the protein radicals that induce lipid peroxidation. $F_2$-isoprostanes formed by this lipid peroxidation are highly potent constrictors of cerebral arterioles. The present inventors have demonstrated a more than 5 fold mean increase in $F_2$-isoprostanes in the cerebrospinal fluid of patients with SAH; this increase is maximal at the time of delayed vasospasm, and the level of increase is a function of the severity of the SAH. We hypothesize that such vasoconstrictors are major contributors to the vasospasm produced by hemoglobin in subarachnoid hemorrhage.

The present inventors have discovered that acetaminophen is a potent inhibitor of hemoprotein-catalyzed lipid peroxidation with an $IC_{50}$ for hemoglobin of 15 µM, which is in the range of plasma levels resulting from therapeutic doses of the drug in humans. Acetaminophen acts by reducing the ferryl-oxo radical form of the heme, and thereby prevents formation of the hemoprotein radical that initiates lipid peroxidation by hemoglobin as well as by myoglobin. To assess proof of concept in vivo, we determined the effect of acetaminophen in a rat model of rhabdomyolysis in which renal failure is caused by intense vasospasm resulting from myoglobin-catalyzed lipid peroxidation. Acetaminophen blocked lipid peroxidation in this model, and prevented the renal failure with a dose that produced plasma levels in the therapeutic range for humans.

An inhibitor of hemeprotein-catalyzed lipid peroxidation is considered for a number of potential therapeutic targets. These include the renal failure that results from release of myoglobin from skeletal muscle in rhabdomyolysis and the myocardial reperfusion injury associated with release of myoglobin from ischemic cardiomyocytes. Hemoglobin-induced lipid peroxidation is linked to the pathophysiology of the renal failure associated with the massive hemolysis in *Plasmodium falciparum* malaria and of the pulmonary crisis in sickle cell disease, in addition to the vasospasm in subarachnoid hemorrhage.

Subarachnoid hemorrhage has been selected as the initial target for acetaminophen and related inhibitors of hemoglobin-induced lipid peroxidation. This selection is based on the strength of the evidence that lipid peroxidation contributes to the vasospasm in subarachnoid hemorrhage, on the catastrophic consequences of this disease, and particularly on the opportunity to initiate pre-emptive therapy in advance of the delayed vasospasm. The NIH has concurred with this target selection, and is funding a pilot study to assess the extent of acetaminophen's effect on lipid peroxidation in patients with subarachnoid hemorrhage.

Another aspect of the present invention is a strategy for development of even more potent inhibitors. We considered that the inhibition could result from either electron transfer or hydrogen atom transfer to the protoporphyrin radical. Acetaminophen (ApAP) is a phenol and as such it could act as an antioxidant by giving up its phenolic hydrogen atom to a chain-propagating lipid peroxyl radical. The bond dissociation enthalpy (BDE) of the phenolic O—H plays a central role in determining antioxidant efficacy, compounds having lower BDEs generally being better antioxidants. Electron-rich phenols like ApAP also serve as good electron donors, and our findings indicate that electron donation is the likely mechanism by which this compound inhibits hemoprotein-induced lipid peroxidation. The ionization potential (IP) of a molecule reports its ability to donate an electron; the lower the IP, the better the electron donor. Recent advances in computational chemistry permit excellent prediction of BDEs and IPs of ApAP and analogs. Computed BDEs are within a kcal/mol or so of experimentally obtained values and calculated IPs provide excellent comparisons within series of compounds. In Table 1 below are presented the calculated BDEs and IPs of a series of phenolic compounds of the present invention that includes ApAP. What is striking about these data is that there are a number of structurally related molecules that have substantially lower BDEs and IPs than does ApAP. It is our hypothesis that these compounds will be substantially better H atom and electron donors than is ApAP. As a result, such compounds will be better antioxidants in general and better inhibitors of hemoprotein-induced lipid peroxidation in particular than is ApAP. Our investigations with the cyclooxygenases and myoglobin confirm both of these predictions.

Another embodiment of the present invention is methods of COX-1 and COX-2 inhibition, and methods of treating cyclooxygenase mediated indications and/or diseases, including the treatment or alleviation of inflammation and other inflammation associated disorders such as arthritis and neurodegeneration.

Thus, embodiments of the present invention include the below compounds and their methods of use. As one of ordinary skill in the art would readily recognize, the synthesis of the compounds is reasonably straightforward.

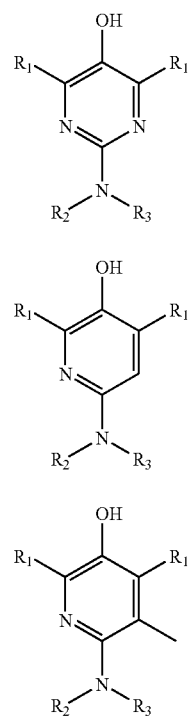

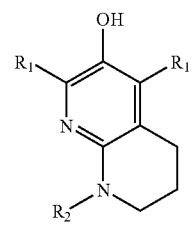

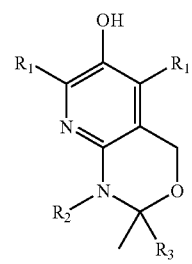

1a, $R_1 = R_2 = R_3 = Me$; b, $R_1 = H\ R_2 = R_3 = Me$; c, $R_1 = R_2 = R_3 = H$
2a, $R_1 = R_2 = R_3 = Me$; b, $R_1 = H\ R_2 = R_3 = Me$; c, $R_1 = R_2 = R_3 = H$
3a, $R_1 = R_2 = R_3 = Me$; b, $R_1 = Me\ R_2 = H\ R_3 = Ethyl$; c, $R_1 = Me\ R_2 = H\ R_3 = Hexyl$; d, $R_1 = Me\ R_2 = H\ R_3 = Hexadecyl$
4a, $R_1 = R_2 = Me$; b, $R_1 = Me\ R_2 = H$; c, $R_1 = Me\ R_2 = Hexadecyl$
5a, $R_1 = R_2 = R_3 = Me$; b, $R_1 = Me\ R_2 = H$; c, $R_1 = Me\ R_2 = Hexadecyl$ Further examples of compounds of the present invention include the following:

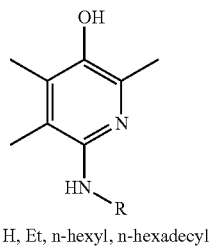

Compound 1

R = H, Et, n-hexyl, n-hexadecyl

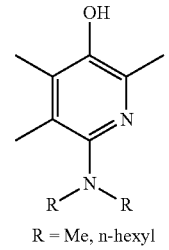

Compound 2

R = Me, n-hexyl

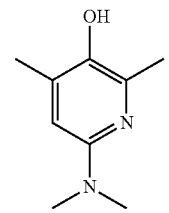

Compound 3

-continued
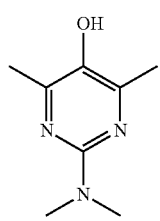
Compound 4
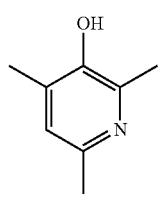
Compound 5
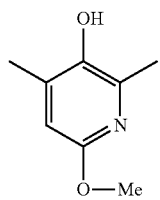
Compound 6
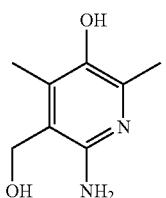
Compound 7
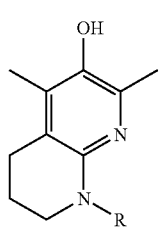
R = H, Me
Compound 8
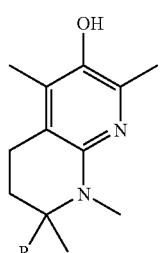
R = H, Me, n-hexyl
-continued
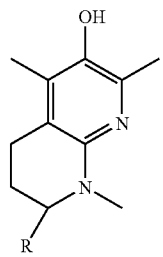
R = t-Bu, n-butyl
Compound 10
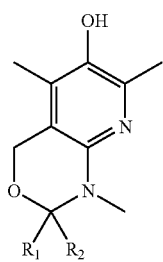
R = R2 = Me
R1 = Me, R2 = n-butyl
R1 = R2 = n-hexyl
Compound 11
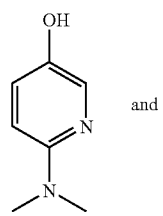
and
Compound 12
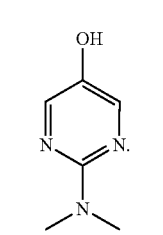
Compound 13
TABLE 1
Additional Embodiments of the Invention
| BDE | 82.5 | 83.2 | 83.7 | 77.0 | 78.3 | 73.5 | 74.1 | (kcal/mol) |
|---|---|---|---|---|---|---|---|---|
| IP | 176 | 184 | 193 | 164 | 175 | 158 | 167 | (kcal/mol) |

TABLE 1-continued

Additional Embodiments of the Invention

The first phase of synthesis and evaluation of additional inhibitors is based on the premise that success in treating diseases resulting from hemoprotein-catalyzed lipid peroxidation will require intervention at the radical initiation step. Thus, aspects of the present invention focus on aqueous soluble agents with improved potency in reducing the hemoprotein protoporphyrin radical, building on the advances in potency already achieved with the lead compounds in this series.

The process of radical initiation and subsequent propagation is subject to potential inhibition at multiple steps, and it has dual amplification mechanisms. It is probably best considered as occurring at an aqueous-lipid phase interface, with the hemoprotein in the aqueous phase, and with hemoprotein radicals eliciting radical formation at the interface with the lipid phase to initiate chain propagation in that phase.

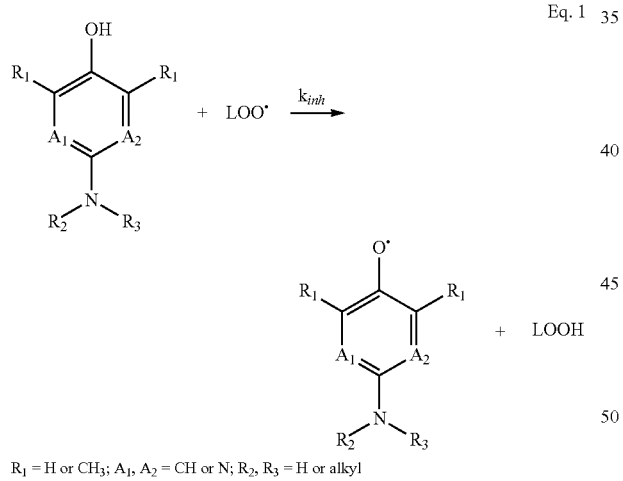

Eq. 1

$R_1$ = H or $CH_3$; $A_1$, $A_2$ = CH or N; $R_2$, $R_3$ = H or alkyl

Phenolic Antioxidants/Reducing Agents of the Present Invention.

Antioxidants, most commonly substituted phenols, effectively intercept peroxyls by transferring the phenolic H-atom to a propagating peroxyl radical, with a rate constant $k_{inh}$ that is faster than that of chain propagation. The most famous example of a phenolic antioxidant is vitamin E ($\alpha$-tocopherol, $\alpha$-TOH) nature's hydrophobic defense against radical chain oxidation.

Compounds of the present invention have a higher $k_{inh}$ and serve as better antioxidants than $\alpha$-TOH in chemical tests. The critical antioxidant step is shown in Equation 1, the larger the $k_{inh}$, the better the antioxidant. The simple pyridinol 2a shown below is nearly 5 times better than $\alpha$-TOH as an antioxidant and the bicyclic compounds 3a and 4a are over 20 times better than the vitamin. ApAP, on the other hand, is a poor antioxidant compared to $\alpha$-TOH, its rate constant for inhibition being 100-fold less than that of $\alpha$-TOH.

Relative Potency:

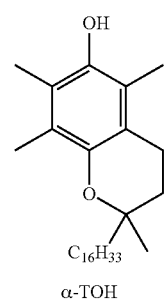

1

$\alpha$-TOH

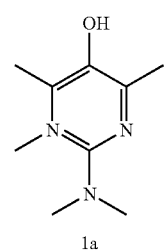

2

1a

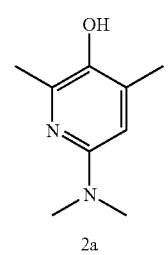

5

2a

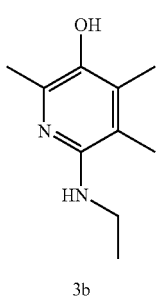

3b

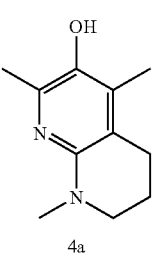

4a

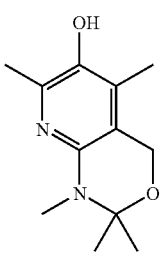

5a

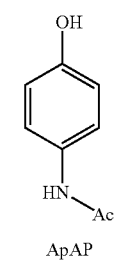

ApAP

Structural characteristics that make the pyridinol and pyrimidinol compounds good antioxidants also promise to make them good inhibitors of hemoprotein induced lipid peroxidation. Antioxidant activity and heme reduction efficacy both depend on the electron donor character of substituents on the phenol. Compounds in the series of pyridinols and pyrimidinols and the bicyclic compounds 4 and 5 are more electron-rich than ApAP and thus they are better antioxidants and promise to be more potent reductants of reactive heme-oxo species such as $O=Fe(IV)PP^+$ than is ApAP.

Also included in the scope of the present invention are pharmaceutical compositions comprising compounds of the present invention, as well as their methods of use for treating patients in need thereof.

With respect to the compounds of the present invention, the following compound,

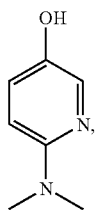

N-dimethyl-pyrimidinol, especially has been found to have promising characteristics; it is 14 times more potent in reducing ferryl myoglobin than is acetaminophen, 10 times more potent as an inhibitor of PGHS-1 and -2, and it is not cytotoxic in a HepG2 cell line stimulated with ethanol in which acetaminophen is toxic.

In another aspect of the present invention, the compounds of the present invention are resveratrole, derivatives, and analogs thereof. The term "resveratrol" is intended to mean either the cis-isomer of resveratrol, the trans-isomer of resveratrol, or a mixture of the two isomers. The term is also intended to include both the naturally occurring active agent and the compound as it may be chemically synthesized in the laboratory.

Resveratrol (3,5,4'-trihydroxystilbene) has been identified as a constituent not only of grape skins (Soleas et al. (1995) Am. J. Enol. Vitic. 46(3):346-352) but has also been found to be present in ground nuts, eucalyptus, and other plant species. Goldberg et al. (1995), Am. J. Enol. Vitic. 46(2): 159-165. A great deal of interest has been focused on the compound's antifungal activity and its correlation with resistance to fungal infection. Id at 159. Resveratrol may be obtained commercially (typically as the trans isomer, e.g. from the Sigma Chemical Company, St. Louis, Mo.), or it may be isolated from wine or grape skins, or it may be chemically synthesized. Synthesis is typically carried out by a Wittig reaction linking two substituted phenols through a styrene double bond, as described by Moreno-Manas et al. (1985) Anal. Quim. 81:157-61 and subsequently modified by others (Jeandet et al. (1991) Am. J. Enol. Vitic. 42:41-46; Goldberg et al. (1994) Anal. Chem. 66: 3959-63).

There are more studies concerning trans-resveratrol than the cis isomer; however, the cis isomer also appears to be equally important from a biological standpoint. Numerous uses have been proposed and evaluated for the resveratrol isomers. Jang et al. (1997) Science 275:218-220, show that resveratrol has cancer chemopreventive activity in assays representing three major stages of carcinogenesis. That is, the authors found that the compound: (1) acted as an antioxidant and antimutagen and induced phase II drug-metabolizing enzymes ("anti-initiation" activity); (2) mediated anti-inflammatory effects and inhibited cyclooxygenase and hydroperoxidase ("antipromotion" activity); and (3) induced human promyelocytic leukemia cell differentiation ("antipromotion" activity). In addition, as noted above, resveratrol has been extensively studied for its correlation to the cardiovascular utility of red wine. See, e.g., Bertelli et al., supra; Pace-Asciak et al. (1995), Clinica Chimica Acta 235:207-2191; and Frankel et al. (Apr. 24, 1993), The Lancet 341:1104. Neurologic uses have also been proposed (Lee et al. (1994), Society for Neuroscience Abstracts 20(1-2):1648).

Thus, in one embodiment, then, a method is provided for preventing or treating restenosis in an individual following coronary intervention, comprising treating the individual with a pharmaceutical composition comprising a therapeutically effective amount of an active agent selected from the group consisting of resveratrol and pharmacologically acceptable salts, esters, amides, prodrugs and analogs thereof. Generally, the active agent will be cis-resveratrol, trans-resveratrol, cis-resveratrol glucoside or trans-resveratrol glucoside, and administration will be either oral or parenteral. However, as will be appreciated by those skilled in the art, and as discussed in detail elsewhere herein, other forms of the active agents may also be used, as may a variety of composition types and modes of administration.

In another embodiment, pharmaceutical compositions are provided for carrying out the present therapeutic method. The compositions contain a therapeutically effective amount of an active agent as described above, and pharmacologically acceptable carrier. Preferably, although not necessarily, the compositions are oral dosage forms or liquid formulations suitable for parenteral administration, containing the active agent in unit dosage form.

Thus, the following are compounds of the present invention:

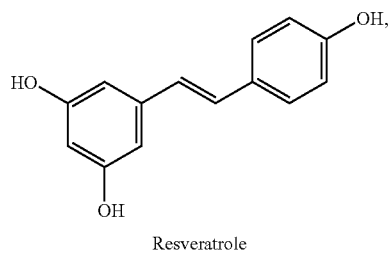

Resveratrole

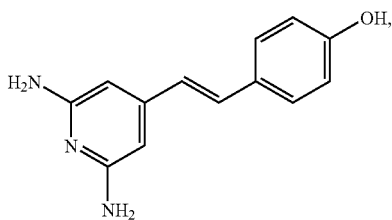

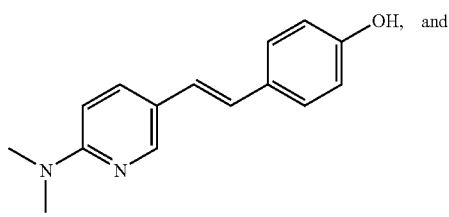

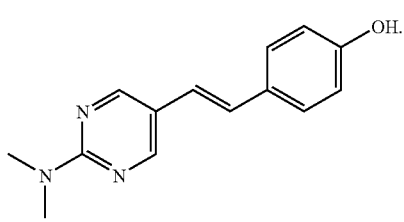

With respect to another embodiment of the present invention, the following compound,

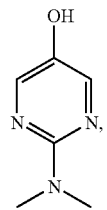

2-(dimethylamino)pyrimidin-5-ol (DM-Pym), is also a particularly highly potent as an inhibitor of PGHS-1 (COX-1) with an $IC_{50}$ of 21 µM. It is more than an order of magnitude more potent as a PGHS-1 inhibitor than is the clinically employed analgesic and anti-pyretic drug, acetaminophen (Tylenol®), which has an $IC_{50}$ of 250 µM in this in vitro system. Additionally, it is equally effective as an inhibitor of PGHS-2 (COX-2) whereas its dimethyl-pyridinol analogue is only a weak inhibitor of PGHS-2. This aspect is important therapeutically, as most of the therapeutic effects of acetaminophen are mediated via its action on PGHS-2.

DM-Pym is also a potent inhibitor of hemoprotein catalyzed lipid peroxidation, the present inventors have demonstrated that acetaminophen is an inhibitor of the lipid peroxidation engendered by the hemoproteins, hemoglobin and myoglobin, in vitro. Moreover, it blocks the renal lipid peroxidation and renal failure produced by rhabdomyolysis. DM-Pym is remarkably more potent than acetaminophen in reducing ferryl myoglobin and thereby reducing the radical that initiates hemoprotein catalyzed lipid peroxidation.

Further, DM-Pym has a more favorable safety profile in cellular toxicity studies in comparison with acetaminophen. The hepatotoxicity of acetaminophen is a major problem with its clinical use; not only is this a cause of liver failure and death from acetaminophen overdose, but it also limits the dose of acetaminophen that can be used for potential indications such as the diseases caused by hemoprotein catalyzed lipid peroxidation. Acetaminophen-induced hepatotoxicity results from an electrophilic metabolite that is formed by the catalysis of acetaminophen by a CYP450 enzyme. Based on this knowledge, a model for acetaminophen toxicity has been developed in which induction of the CYP450 by ethanol in the HepG2 liver cell line makes the cells highly susceptible to the cytotoxic effect of acetaminophen. In this model, in which acetaminophen is shown by us to be cytotoxic, the DM-Pym does not cause cytotoxicity.

A further aspect of the present invention is a biomarker with which to track clinical development. Measurement of $F_2$-isoprostanes in the cerebrospinal fluid (CSF) will be employed as a biomarker for lipid peroxidation engendered by subarachnoid hemorrhage and its inhibition. Analysis of $F_2$-isoprostanes ($F_2$-IsoPs) by GC/MS has been independently validated by an NIEHS study to be the most accurate approach for assessing lipid peroxidation and oxidative stress status in vivo. Thus on aspect of the present invention is a highly validated assay to accurately measure the ability of compounds that will be synthesized to inhibit hemoprotein redox cycling induced lipid peroxidation in vivo. Measurement of $F_2$-IsoPs is utilized both in animal models of hemoprotein-induced lipid peroxidation and subsequently in humans to track clinical development of these compounds. The finding that renal failure due to rhabdomyolysis is associated with lipid peroxidation reflected by elevated $F_2$-IsoPs and that it can be inhibited by acetaminophen greatly supports our hypothesis that $F_2$-IsoPs formed in the CSF in SAH are key mediators of the vasospasm in SAH. To obtain further support for this hypothesis we measured CSF $F_2$-IsoPs in patients with SAH. As indicated in the table below, levels of $F_2$-IsoPs were markedly increased in subarachnoid hemorrhage and the extent of increase was a function of the severity of the subarachnoid bleed (Fisher Grade), and whether the hemorrhage had produced a vegetative state. The highest levels were seen on day 7 which is the time of delayed vasospasm.

| | CSF $F_2$-IsoProstanes (pg/ml) at Peak Value | | | | |
|---|---|---|---|---|---|
| | | SAH Fisher Grade | | | Outcome = |
| | Normal | All SAH | I | II | III or III + IV | Vegetative state |
| Mean ± SE (n) | 8.7 ± 1.2 (10) | 50.0 ± 5.9 (14) | 28.3 (2) | 39.7 (1) | 54.9 ± 6.8 (11) | 79.7 ± 14.1 (3) |

The compounds and compositions of the invention can be administered by any available and effective delivery system including, but not limited to, orally, bucally, parenterally, by inhalation spray, by topical application, by injection, transdermally, or rectally (e.g., by the use of suppositories) in dosage unit formulations containing conventional nontoxic pharmaceutically acceptable carriers, adjuvants, and vehicles, as desired. Parenteral includes subcutaneous injections, intravenous, intramuscular, intrasternal injection, or infusion techniques.

Transdermal compound administration, which is known to one skilled in the art, involves the delivery of pharmaceutical compounds via percutaneous passage of the compound into the systemic circulation of the patient. Topical administration can also involve the use of transdermal administration such as transdermal patches or iontophoresis devices. Other components can be incorporated into the transdermal patches as well. For example, compositions and/or transdermal patches can be formulated with one or more preservatives or bacteriostatic agents including, but not limited to, methyl hydroxybenzoate, propyl hydroxybenzoate, chlorocresol, benzalkonium chloride, and the like. Dosage forms for topical administration of the compounds and compositions can include creams, sprays; lotions, gels, ointments, eye drops, nose drops, ear drops, and the like. In such dosage forms, the compositions of the invention can be mixed to form white, smooth, homogeneous, opaque cream or lotion with, for example, benzyl alcohol 1% or 2% (wt/wt) as a preservative, emulsifying wax, glycerin, isopropyl palmitate, lactic acid, purified water and sorbitol solution. In addition, the compositions can contain polyethylene glycol 400. They can be mixed to form ointments with, for example, benzyl alcohol 2% (wt/wt) as preservative, white petrolatum, emulsifying wax, and tenox II (butylated hydroxyanisole, propyl gallate, citric acid, propylene glycol). Woven pads or rolls of bandaging material, e.g., gauze, can be impregnated with the compositions in solution, lotion, cream, ointment or other such form can also be used for topical application. The compositions can also be applied topically using a transdermal system, such as one of an acrylic-based polymer adhesive with a resinous crosslinking agent impregnated with the composition and laminated to an impermeable backing.

Solid dosage forms for oral administration can include capsules, tablets, effervescent tablets, chewable tablets, pills, powders, sachets, granules and gels. In such solid dosage forms, the active compounds can be admixed with at least one inert diluent such as sucrose, lactose or starch. Such dosage forms can also comprise, as in normal practice, additional substances other than inert diluents, e.g., lubricating agents such as magnesium stearate. In the case of capsules, tablets, effervescent tablets, and pills, the dosage forms can also comprise buffering agents. Soft gelatin capsules can be prepared to contain a mixture of the active compounds or compositions of the invention and vegetable oil. Hard gelatin capsules can contain granules of the active compound in combination with a solid, pulverulent carrier such as lactose, saccharose, sorbitol, mannitol, potato starch, corn starch, amylopectin, cellulose derivatives of gelatin. Tablets and pills can be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

Suppositories for vaginal or rectal administration of the compounds and compositions of the invention, such as for treating pediatric fever and the like, can be prepared by mixing the compounds or compositions with a suitable nonirritating excipient such as cocoa butter and polyethylene glycols which are solid at room temperature but liquid at rectal temperature, such that they will melt in the rectum and release the drug.

Injectable preparations, for example, sterile injectable aqueous or oleaginous suspensions can be formulated according to the known art using suitable dispersing agents, wetting agents and/or suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be used are water, Ringer's solution, and isotonic sodium chloride solution. Sterile fixed oils are also conventionally used as a solvent or suspending medium.

The compositions of this invention can further include conventional excipients, i.e., pharmaceutically acceptable organic or inorganic carrier substances suitable for parenteral application which do not deleteriously react with the active compounds. Suitable pharmaceutically acceptable carriers include, for example, water, salt solutions, alcohol, vegetable oils, polyethylene glycols, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds. For parenteral application, particularly suitable vehicles consist of solutions, preferably oily or aqueous solutions, as well as suspensions, emulsions, or implants. Aqueous suspensions may contain substances which increase the viscosity of the suspension and include, for example, sodium carboxymethyl cellulose, sorbitol and/or dextran. Optionally, the suspension may also contain stabilizers.

The composition, if desired, can also contain minor amounts of wetting agents, emulsifying agents and/or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, and the like.

Various delivery systems are known and can be used to administer the compounds or compositions of the invention, including, for example, encapsulation in liposomes, microbubbles, emulsions, microparticles, microcapsules and the like. The required dosage can be administered as a single unit or in a sustained release form.

The bioavailabilty of the compositions can be enhanced by micronization of the formulations using conventional techniques such as grinding, milling, spray drying and the like in the presence of suitable excipients or agents such as phospholipids or surfactants.

Of course, the compounds and compositions of the invention can be formulated as pharmaceutically acceptable salt forms. Pharmaceutically acceptable salts include, for example, alkali metal salts and addition salts of free acids or free bases. The nature of the salt is not critical, provided that it is pharmaceutically-acceptable. Suitable pharmaceutically-acceptable acid addition salts may be prepared from an inorganic acid or from an organic acid. Examples of such inorganic acids include, but are not limited to, hydrochloric, hydrobromic, hydroiodic, nitric, carbonic, sulfuric and phosphoric acid and the like. Appropriate organic acids include, but are not limited to, aliphatic, cycloaliphatic, aromatic, heterocyclic, carboxylic and sulfonic classes of organic acids, such as, for example, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, algenic, .beta.-hydroxybutyric, cyclohexylaminosulfonic, galactaric and galacturonic acid and the like. Suitable pharmaceutically-acceptable base addition salts include, but are not limited to, metallic salts made from aluminum, calcium, lithium, magnesium, potassium, sodium and zinc or organic salts made from primary, secondary and tertiary amines, cyclic amines, N,N'-dibenzylethylenediamine, chloroprocaine, choline, diethanolamine, ethylenediamine, meglumine (N-methylglucamine) and procaine and the like. All of these salts may be prepared by conventional means from the corresponding compound by reacting, for example, the appropriate acid or base with the compound.

While individual needs may vary, determination of optimal ranges for effective amounts of the compounds and/or compositions is within the skill of the art. Generally, the dosage required to provide an effective amount of the compounds and compositions, which can be adjusted by one of ordinary skill in the art, will vary depending on the age, health, physical condition, sex, diet, weight, extent of the dysfunction of the recipient, frequency of treatment and the nature and scope of the dysfunction or disease, medical condition of the patient, the route of administration, pharmacological considerations such as the activity, efficacy, pharmacokinetic and toxicology profiles of the particular compound used, whether a drug delivery system is used, and whether the compound is administered as part of a drug combination.

The amount of a given compound or composition of the invention that will be effective in the treatment of a particular disorder or condition will depend on the nature of the disorder or condition, and can be determined by standard clinical techniques, including reference to Goodman and Gilman, supra; The Physician's Desk Reference, Medical Economics Company, Inc., Oradell, N.J., 1995; and Drug Facts and Comparisons, Inc., St. Louis, Mo., 1993. The precise dose to be used in the formulation will also depend on the route of administration, and the seriousness of the disease or disorder, and should be decided by the physician and the patient's circumstances.

EXAMPLES

The following examples are presented for exemplary purposes only. As such, they are to be construed as representing embodiments or aspects of the present invention, and not to be construed as being limiting thereof.

Example 1

This example shows inhibition of PGHS-1 by N-dimethyl pyridinol and N-dimethylpyrimidinol analogues of acetaminophen (ApAP). See FIG. 1. Hematin-reconstituted PGHS-1 5.4 nM in Tris HCl 100 mM, pH 8.0, 500 µM phenol, was pre-incubated with acetaminophen (ApAP), 2-(dimethylamino)pyrimidin-5-ol (DM-Pym) or 6-(dimethylamino)pyridin-3-ol (DM-Pyr) at varying concentrations at 37° C. for 20 minutes. At this time the reaction was initiated by addition of 0.5 µM of [14C] arachidonic acid. After 8 seconds, the reaction was stopped by adding an ice cold mixture of diethyl ether/methanol/4.0 M citric acid. PGHS-1 activity was expressed as percent oxidation of arachidonic acid compared with control where no inhibitor was added. Each data point represents the mean±S.E.M of six values.

Example 2

Figure 2:
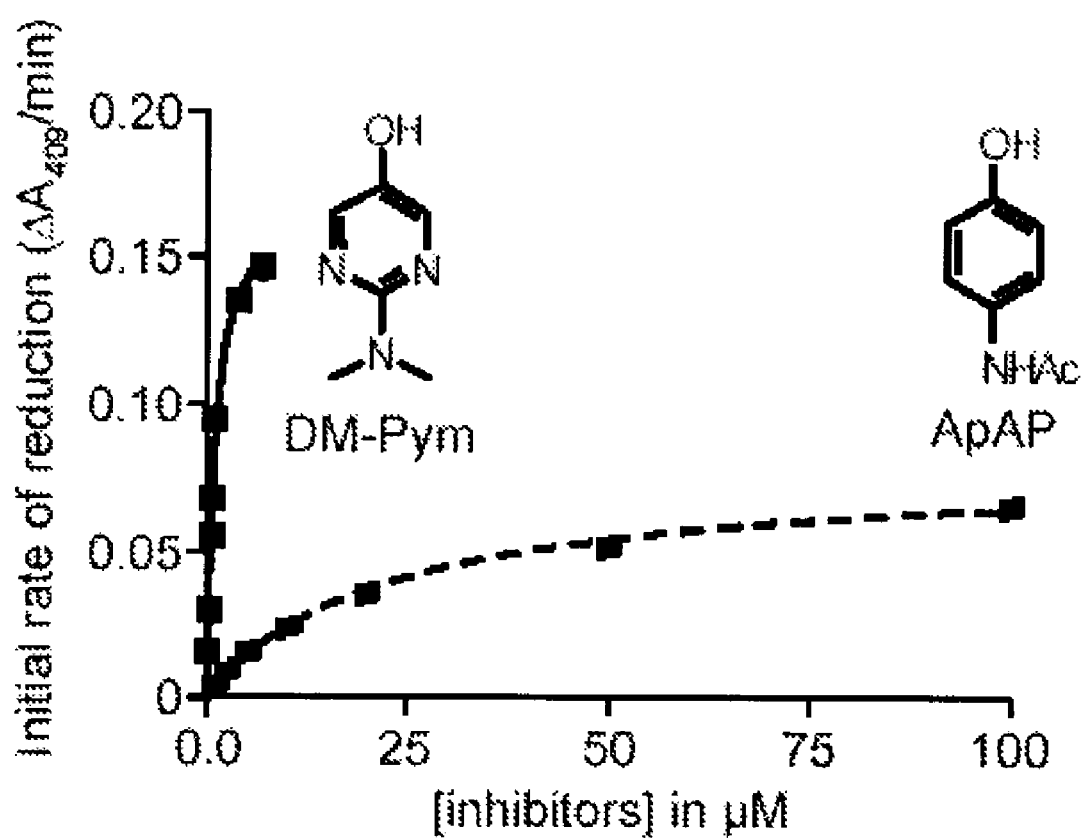
FIG. 2 is a graph that shows the effect of ApAP and DM-Pym analog on the initial rate of reduction of ferryl-myoglobin.

This example shows the effect of ApAP and DM-Pym analog on the initial rate of reduction of ferryl-myoglobin. See FIG. 2. Reduction from ferryl to ferric myoglobin by acetaminophen (ApAP, dashed line) or by 2-(dimethylamino)pyrimidin-5-ol (DM-Pym, plain line) was monitored by recording visible spectra between 350 and 650 nm. Ferryl myoglobin was generated by incubating ferric myoglobin 10 µM in PBS with 10 µM hydrogen peroxide until there was no more change in the peak at 421 nm. At this time, the analogs were added to the cuvette at the final concentrations indicated and spectra were recorded every 15 sec for 2 min. The initial rate of reduction was calculated as the variation of absorbance at 409 nm in the first two minutes after adding the analogs. In this period of time the rates of reduction were linear for each concentration of analog.

Example 3

Figure 3:
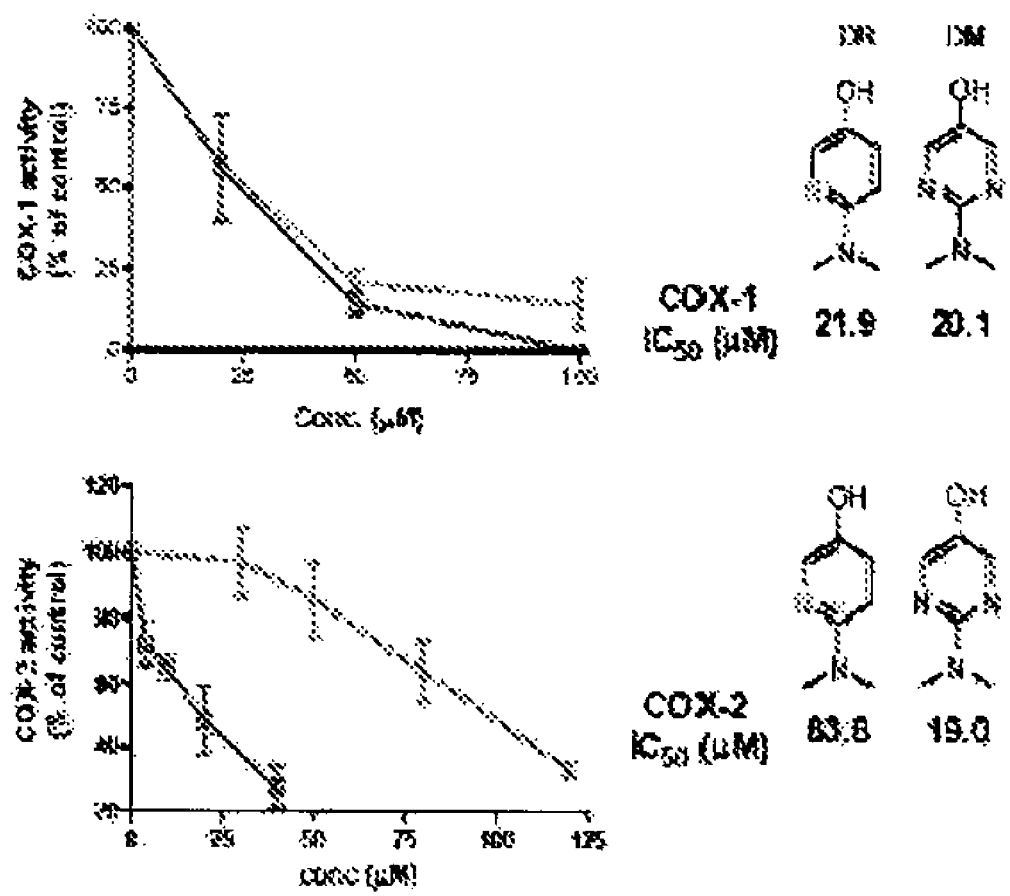
FIG. 3 is a graph that shows the selective inhibition of COX isoforms by acetaminophen analogs of the present invention.

This example shows the selective inhibition of COX isoforms by acetaminophen analogs. Hematin-reconstituted COX-1 (5.4 nM) or COX-2 (10.8 nM) in Tris HCl 100 mM, pH 8.0, 500 µM phenol, was pre-incubated with N-dimethyl pyrimidinol (DM, plain line) or N-dimethyl pyridinol (DR, dashed line) at varying concentrations at 37° C. for 20 minutes. See FIG. 3. At this time the reaction was initiated by addition of 0.5 µM of [14C] arachidonic acid. After 8 seconds, the reaction was stopped by adding an ice cold mixture of diethyl ether/methanol/4.0 M citric acid. PGHS-1 activity was expressed as percent oxidation of arachidonic acid compared with control where no inhibitor was added. Each data point represents the mean±S.E.M of six values.

Example 4

Figure 4:
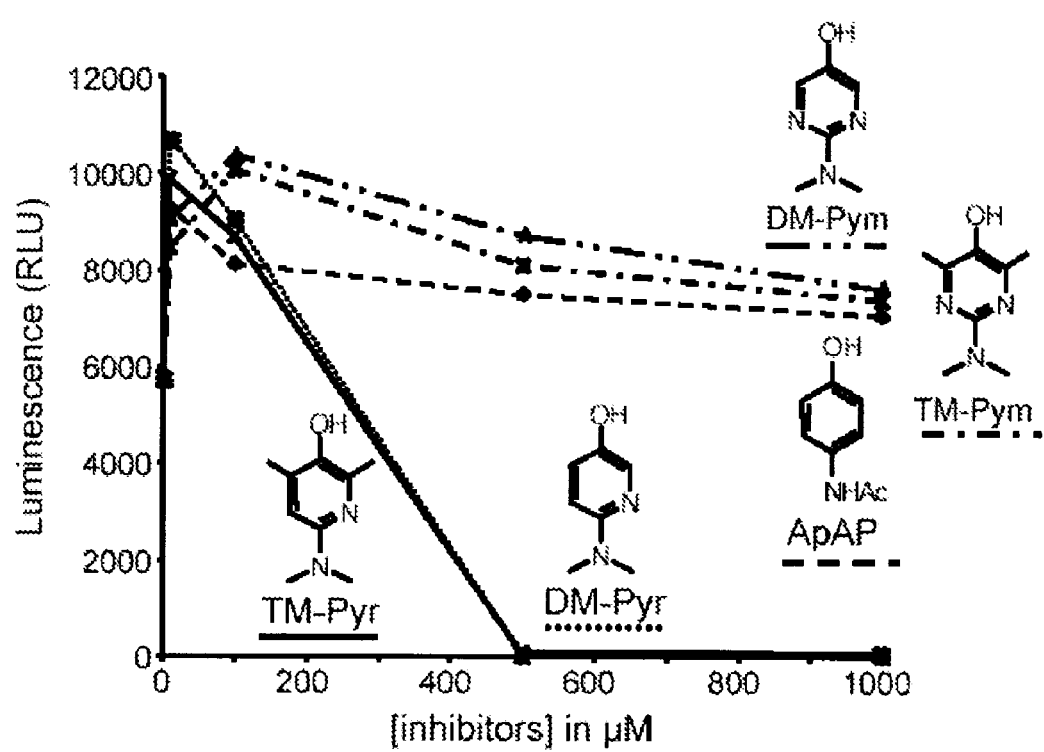
FIG. 4 is a graph that shows cytotoxicity of acetaminophen analogs of the present invention in HepG2 cells.

This example shows cytotoxicity of acetaminophen analogs in HepG2 cells. See FIG. 4. HepG2 were plated in multiple 96-well plates at 2×104 cells per well and pretreated with vehicle only (0 µM inhibitors), or different concentrations of acetaminophen (ApAP), 2-(dimethylamino)pyrimidin-5-ol (DM-Pym) or 6-(dimethylamino)pyridin-3-ol (DM-Pyr), 2-(dimethylamino)-4,6-dimethylpyrimidin-5-ol (TM-Pym) or 6-(dimethylamino)-2,4-dimethylpyridin-3-ol (TM-Pyr). Cell viability after 24 h was determined by measuring ATP levels by luminescence assay.

Example 5

Figure 5:
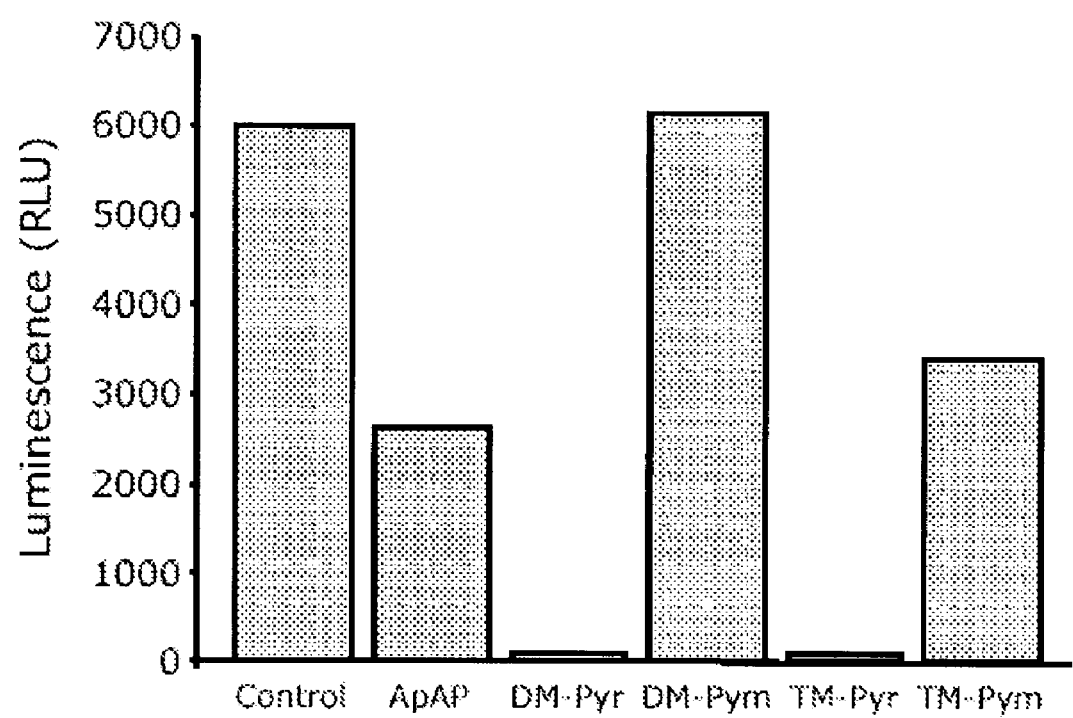
FIG. 5 is a graph that shows the effect of ethanol on cytotoxicity of acetaminophen analogs in HepG2 cells.

This example shows the effect of ethanol on cytotoxicity of acetaminophen analogs in HepG2 cells. See FIG. 5. HepG2 were plated in multiple 96-well plates at 2×104 cells per well and pretreated with ethanol 100 µM for 2 hours. At this time, vehicle (0 µM inhibitors), or acetaminophen (ApAP), 2-(dimethylamino)pyrimidin-5-ol (DM-Pym) or 6-(dimethylamino)yridine-3-ol (DM-Pyr), 2-(dimethylamino)-4,6-dimethylpyrimidin-5-ol (TM-Pym) or 6-(dimethylamino)-2,4-dimethylpyridin-3-ol (TM-Pyr) were added at 2 mM final concentration. Cell viability after 24 h was determined by measuring ATP levels by luminescence assay.

The invention thus being described, it will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. Particularly, it should be obvious that the embodiments described can be modified without departing from the spirit of the present invention.

Throughout this disclosure, various publications are referenced. All references cited herein are expressly incorporated herein by reference in their entirety and are considered to be part of this disclosure. Of course, all attachments submitted with the Specification are incorporated herein by reference in their entirety and are intended to be considered part of the present patent application.

We claim:

1. A method for treating, or reducing oxidative damage in a mammalian subject comprising administering a therapeutically effective amount of a compound of the following formula:

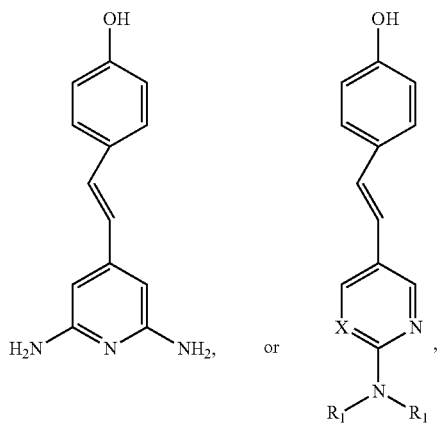

wherein
X is N or C, with the C being unsubstituted or substituted with H or alkyl;
R$_1$ is H or alkyl;
or a pharmaceutically acceptable salt thereof.

2. The method of claim 1, wherein the therapeutically effective amount is a heme-induced lipid peroxidation inhibiting amount.

3. A method of treating isoprostane-mediated tissue damage in a mammalian subject comprising administering a therapeutically effective amount of a compound of the following formula:

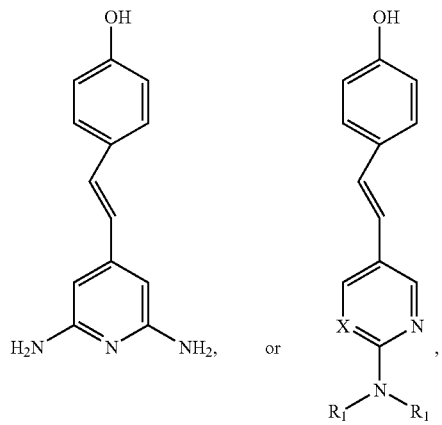

wherein
X is N or C, with the C being unsubstituted or substituted with H or alkyl;
R$_1$ is H or alkyl; or a pharmaceutically acceptable salt thereof.

4. The method of claim 3, wherein the therapeutically effective amount is an isoprostane synthesis inhibiting amount.

5. A method for inhibiting cyclooxygenase or prostaglandin H synthase enzymes, comprising administering a therapeutically effective amount of a compound of the following formula:

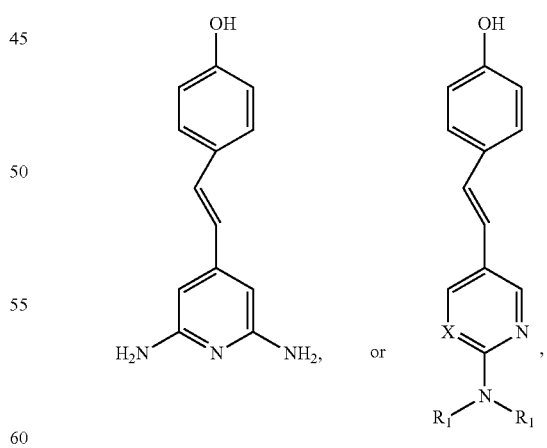

wherein
X is N or C, with the C being unsubstituted or substituted with H or alkyl;
R$_1$ is H or alkyl; or a pharmaceutically acceptable salt thereof.

6. A compound of the following formula:

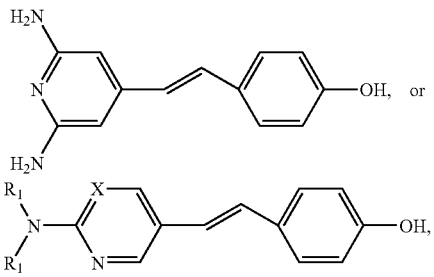

wherein X is N or C, with the C being unsubstituted or substituted with H or alkyl; $R_1$ is H or alkyl; and pharmaceutically acceptable salts thereof.

7. A compound of claim 6, of the following formula:

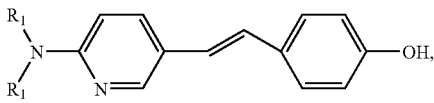

wherein $R_1$ is H or alkyl; or a pharmaceutically acceptable salt thereof.

8. A compound of claim 6, of the following formula:

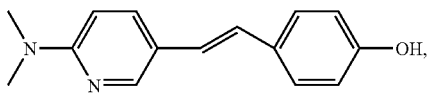

or a pharmaceutically acceptable salt thereof.

9. A compound of claim 6, of the following formula:

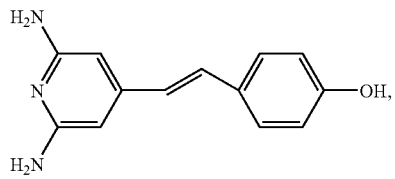

or a pharmaceutically acceptable salt thereof.

10. A composition comprising a compound of claim 6, and a pharmaceutically acceptable carrier.

11. A composition of claim 10, wherein the compound is

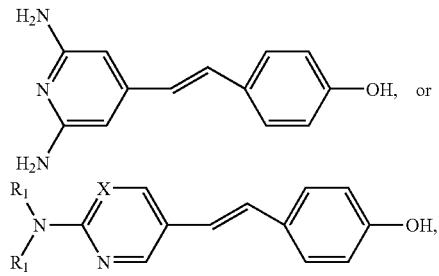

wherein X is N or C, with the C being unsubstituted or substituted with H or alkyl; $R_1$ is H or alkyl; and pharmaceutically acceptable salts thereof.

* * * * *